(12) United States Patent
Boudreaux et al.

(10) Patent No.: US 10,702,296 B2
(45) Date of Patent: Jul. 7, 2020

(54) ULTRASONIC SURGICAL INSTRUMENT WITH COOLING CONDUIT

(71) Applicant: Ethicon Endo-Surgery, LLC, Guaynabo, PR (US)

(72) Inventors: Chad P. Boudreaux, Cincinnati, OH (US); Jeffrey D. Messerly, Cincinnati, OH (US); Kevin Bash, Cincinnati, OH (US); David A. Witt, Maineville, OH (US); Cory G. Kimball, Hamilton, OH (US)

(73) Assignee: Ethicon LLC, Guaynabo, PR (US)

( * ) Notice: Subject to any disclaimer, the term of this patent is extended or adjusted under 35 U.S.C. 154(b) by 622 days.

(21) Appl. No.: 15/163,811

(22) Filed: May 25, 2016

(65) Prior Publication Data

US 2017/0340344 A1    Nov. 30, 2017

(51) Int. Cl.
*A61B 17/32* (2006.01)
*A61B 17/16* (2006.01)
*A61B 18/00* (2006.01)

(52) U.S. Cl.
CPC .. *A61B 17/320068* (2013.01); *A61B 17/1644* (2013.01); *A61B 2017/1651* (2013.01); *A61B 2017/320072* (2013.01); *A61B 2017/320075* (2017.08); *A61B 2017/320084* (2013.01); *A61B 2017/320098* (2017.08); *A61B 2018/00029* (2013.01); *A61B 2217/007* (2013.01)

(58) Field of Classification Search
CPC ..... A61B 17/320068; A61B 17/22004–22029; A61B 2017/32007; A61B 18/0206; A61B 2018/00589–00601; A61C 3/03; A61M 25/0067; A61M 25/007; A61F 9/00745
See application file for complete search history.

(56) References Cited

U.S. PATENT DOCUMENTS

| 2,874,470 A | * | 2/1959 | Richards | .................. | A61C 1/07 |
| | | | | | 310/26 |
| 4,587,958 A | * | 5/1986 | Noguchi | .......... | A61B 17/22012 |
| | | | | | 310/316.01 |
| 4,747,820 A | * | 5/1988 | Hornlein | ........ | A61B 17/320068 |
| | | | | | 604/22 |

(Continued)

FOREIGN PATENT DOCUMENTS

WO    WO 2013/190937 A1    12/2013

OTHER PUBLICATIONS

U.S. Appl. No. 61/410,603, filed Nov. 5, 2010.
International Search Report and Written Opinion dated Jul. 21, 2017 for Application No. PCT/US2017/032622, 13 pgs.

*Primary Examiner* — Tan-Uyen T Ho
*Assistant Examiner* — Charles M Wei
(74) *Attorney, Agent, or Firm* — Frost Brown Todd LLC

(57) ABSTRACT

An apparatus includes a body assembly, an acoustic waveguide, an ultrasonic blade, and a liquid dispensing feature. The ultrasonic blade is positioned distally relative to the body assembly. The ultrasonic blade is in acoustic communication with the acoustic waveguide. The liquid dispensing feature is positioned distally relative to the body assembly. The liquid dispensing feature is positioned adjacent to the ultrasonic blade. The liquid dispensing feature is configured to deliver a flow of cooling liquid to the ultrasonic blade.

19 Claims, 14 Drawing Sheets

(56) References Cited

U.S. PATENT DOCUMENTS

| | | | | |
|---|---|---|---|---|
| 4,886,060 | A * | 12/1989 | Wiksell | A61B 17/320068 606/39 |
| 5,062,827 | A * | 11/1991 | Wiksell | A61F 9/00745 601/2 |
| 5,162,044 | A * | 11/1992 | Gahn | A61F 9/00745 604/22 |
| 5,199,943 | A * | 4/1993 | Wypych | A61F 9/00745 604/22 |
| 5,254,082 | A * | 10/1993 | Takase | A61B 17/320068 604/119 |
| 5,322,055 | A | 6/1994 | Davison et al. | |
| 5,359,996 | A * | 11/1994 | Hood | A61B 17/320068 604/22 |
| 5,527,276 | A * | 6/1996 | Bruce | A61B 17/3415 604/506 |
| 5,873,873 | A | 2/1999 | Smith et al. | |
| 5,980,510 | A | 11/1999 | Tsonton et al. | |
| 6,214,017 | B1 * | 4/2001 | Stoddard | A61B 17/320068 606/128 |
| 6,325,811 | B1 | 12/2001 | Messerly | |
| 6,379,371 | B1 * | 4/2002 | Novak | A61B 17/320068 30/123.3 |
| 6,443,969 | B1 * | 9/2002 | Novak | A61B 17/320068 606/169 |
| 6,524,251 | B2 | 2/2003 | Rabiner et al. | |
| 6,773,444 | B2 | 8/2004 | Messerly | |
| 6,783,524 | B2 | 8/2004 | Anderson et al. | |
| 8,048,095 | B2 * | 11/2011 | Babaev | A61B 17/3203 606/167 |
| 8,348,880 | B2 * | 1/2013 | Messerly | A61B 17/32009 604/22 |
| 8,461,744 | B2 | 6/2013 | Wiener et al. | |
| 8,591,459 | B2 | 11/2013 | Clymer et al. | |
| 8,591,536 | B2 | 11/2013 | Robertson | |
| 8,623,027 | B2 | 1/2014 | Price et al. | |
| 8,986,302 | B2 | 3/2015 | Aldridge et al. | |
| 9,023,071 | B2 | 5/2015 | Miller et al. | |
| 9,320,528 | B2 * | 4/2016 | Voic | A61B 17/142 |
| 9,381,058 | B2 | 7/2016 | Houser et al. | |
| 9,554,809 | B2 | 1/2017 | Lark et al. | |
| 2003/0204199 | A1 * | 10/2003 | Novak | A61B 17/320068 606/169 |
| 2004/0153026 | A1 * | 8/2004 | Mackool | A61F 9/00736 604/22 |
| 2006/0052774 | A1 * | 3/2006 | Garrison | A61B 17/22012 606/42 |
| 2006/0079874 | A1 | 4/2006 | Faller et al. | |
| 2006/0147878 | A1 * | 7/2006 | Tsai | A61C 3/03 433/84 |
| 2007/0191713 | A1 | 8/2007 | Eichmann et al. | |
| 2007/0282333 | A1 | 12/2007 | Fortson et al. | |
| 2008/0200940 | A1 | 8/2008 | Eichmann et al. | |
| 2012/0116265 | A1 | 5/2012 | Houser et al. | |
| 2013/0090576 | A1 | 4/2013 | Stulen et al. | |
| 2015/0005771 | A1 * | 1/2015 | Voic | A61B 17/320068 606/79 |
| 2015/0148832 | A1 | 5/2015 | Boudreaux et al. | |
| 2016/0106455 | A1 | 4/2016 | Aldridge et al. | |
| 2017/0340339 | A1 * | 11/2017 | Madan | A61B 17/1644 |
| 2017/0340345 | A1 * | 11/2017 | Yates | A61B 17/3211 |

\* cited by examiner

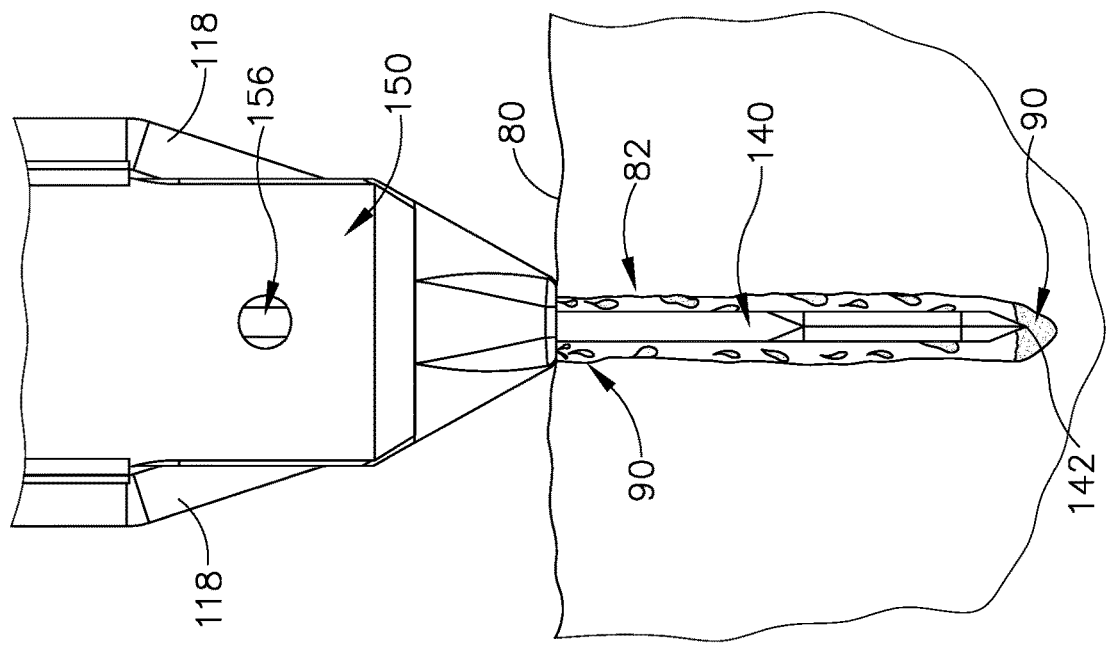
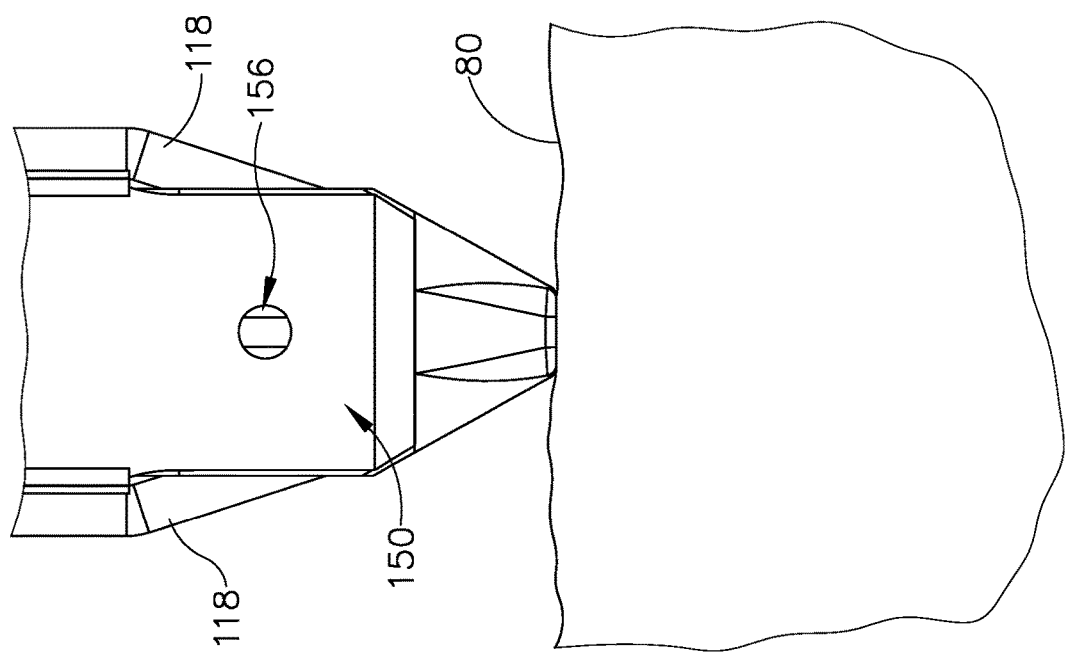
Fig. 11B
Fig. 11A

ULTRASONIC SURGICAL INSTRUMENT WITH COOLING CONDUIT

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,632,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Ultrasonic surgical instruments such as those described in the above-cited references may be primarily used to sever and/or seal soft tissue. However, it may be desirable to use an ultrasonic surgical instrument to cut bone, in addition to or as an alternative to cutting/sealing soft tissue. Cutting bone with an ultrasonic surgical instrument may generate more heat than cutting/sealing soft tissue with an ultrasonic surgical instrument. Unless properly addressed, this additional heat may cause undesirable effects, such as damage (e.g., necrosis) to adjacent bone and/or tissue; and/or damage to the ultrasonic blade.

Some conventional ultrasonic surgical instruments may be configured to use fluid to cool an ultrasonic blade. Examples of such instruments are described in U.S. Pub. No. 2015/0148832, entitled "Features to Apply Fluid to an Ultrasonic Blade of a Surgical Instrument," published May 28, 2015, issued as U.S. Pat. No. 10,034,685 on Jul. 31, 2018, the disclosure of which is incorporated by reference herein. Other examples of ultrasonic surgical instruments that are configured to communicate fluid are described in U.S. Pub. No. 2013/0090576, entitled "Surgical Instrument with Ultrasonic Waveguide Defining a Fluid Lumen, published Apr. 11, 2013, now abandoned, the disclosure of which is incorporated by reference herein; and U.S. Pat. No. 8,591,459, entitled "Use of Biomarkers and Therapeutic Agents with Surgical Devices," issued Nov. 26, 2013, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 11A depicts a side elevational view of the working end of FIG. 9A, with the cooling sheath in the distal position, and with the working end in an initial state of engagement with a bone surface;

FIG. 11B depicts a side elevational view of the working end of FIG. 9A, with the cooling sheath in the proximal position, and with a blade of the working end disposed in bone;

Figure 1:
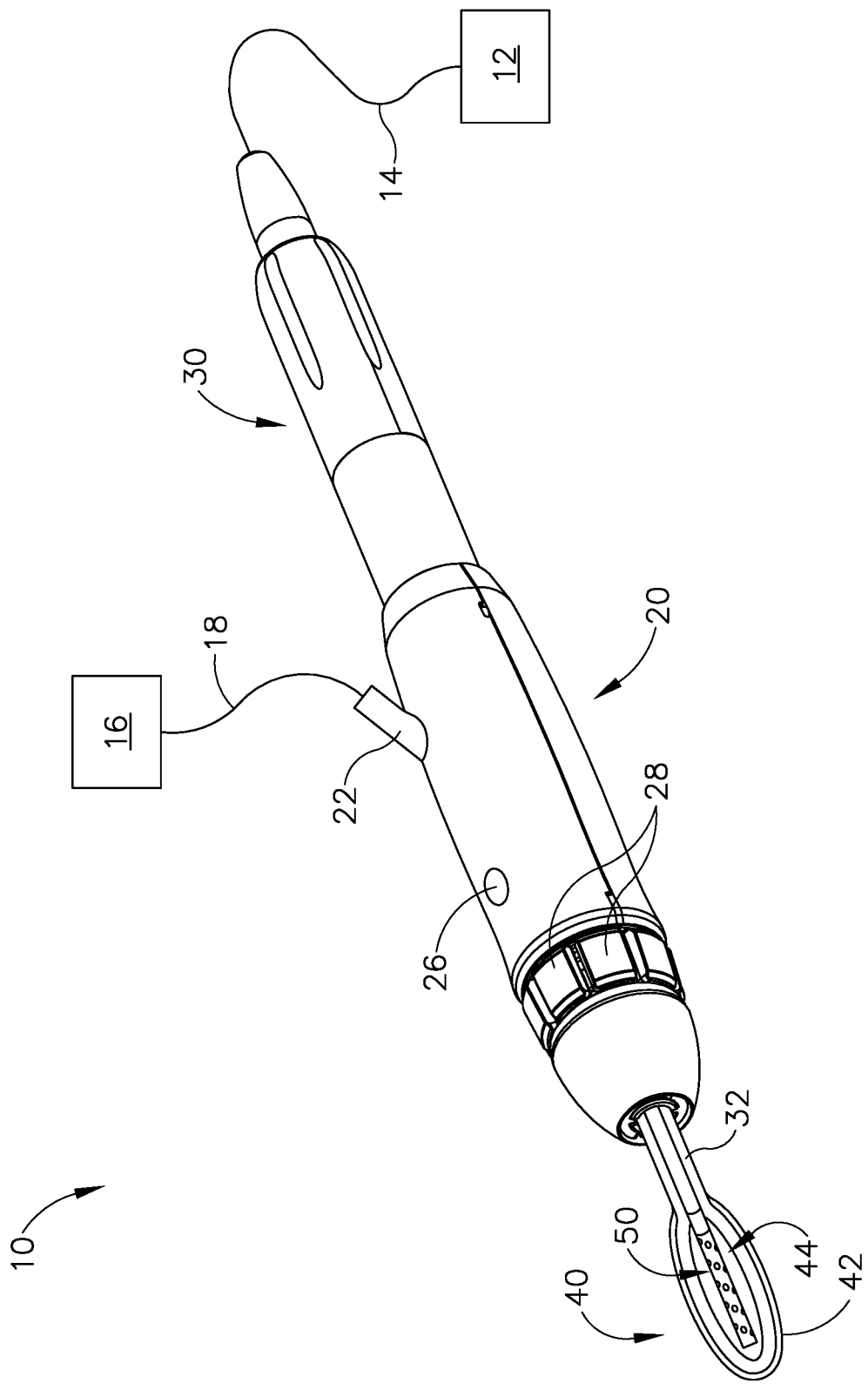
FIG. 1 depicts a perspective view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument with Fixed Position Liquid Cooling Feature FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously.

Instrument (10) of the present example comprises a handle assembly (20), an ultrasonic transducer assembly (30), an ultrasonic blade (40), and a liquid dispensing feature (50). Handle assembly (20) is configured to be grasped using a pencil grip, though some operators may choose to grasp handle assembly (20) in some other fashion (e.g., using a power grip, etc.). Handle assembly (20) includes a fluid port (22), a fluid switch (26), and a plurality of activation buttons (28).

Fluid port (22) is configured to couple with a fluid conduit (18), which is further in communication with a fluid source (16). Fluid conduit (18) may comprise a flexible tube and/or any other kind of conduit (18). By way of example only, fluid conduit (18) may be coupled with fluid port (22) via a luer fitting and/or any other suitable kind(s) of connection features. Fluid source (16) may comprise a soft container (e.g., a bag), a hard container (e.g., a box or canister), or have any other suitable configuration. In some versions, fluid source (16) is not pressurized, such that fluid flows from fluid source (16) to port under the influence of gravity. In some other versions, fluid source (16) is pressurized. For instance, fluid source (16) may comprise a pump or other pressurizing assembly. As another merely illustrative example, fluid source (16) may contain a pre-pressurized fluid.

In any of the foregoing versions, fluid switch (26) is operable to selectively control the flow of fluid from fluid source (16) to liquid dispensing feature (50). For instance, fluid switch (26) may be operable to actuate a valve to transition the valve between an open state and a closed state. In some other versions, fluid switch (26) is omitted and the flow of fluid from fluid source (16) to liquid dispensing feature (50) is either constant or is regulated automatically. Various components and configurations that may be used to selectively restrict the flow of fluid from fluid source (16) to liquid dispensing feature (50) will be apparent to those of ordinary skill in the art in view of the teachings herein. It should also be understood that any suitable fluids may be communicated from fluid source (16) to liquid dispensing feature (50) to cool a surgical site, including but not limited to saline.

Ultrasonic transducer assembly (30) extends proximally from handle assembly (20) and is coupled with a generator (12) via a cable (14), such that transducer assembly (30) receives electrical power from generator (12). Piezoelectric elements in transducer assembly (30) convert that electrical power into ultrasonic vibrations. Generator (12) may include a power source and control module that is configured to provide a power profile to transducer assembly (30) that is particularly suited for the generation of ultrasonic vibrations through transducer assembly (30). By way of example only, generator (12) may comprise a GEN04 or GEN11 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. In versions where generator (12) is capable of driving various different kinds of ultrasonic surgical instruments (e.g., with different resonant frequencies), handle assembly (20) may include an EEPROM or some other feature that identifies the type of ultrasonic surgical instrument (10) for generator (12), such that generator (12) may automatically select and deliver the appropriate power profile based on the identified type of ultrasonic surgical instrument (10).

It should also be understood that at least some of the functionality of generator (12) may be integrated into handle assembly (20), and that handle assembly (20) may even include a battery or other on-board power source such that cable (14) is omitted. Still other suitable forms that generator (12) may take, as well as various features and operabilities that generator (12) may provide, will be apparent to those of ordinary skill in the art in view of the teachings herein.

In the present example, transducer assembly (30) is activated in response to the operator actuating at least one button (28) of handle assembly (20). Buttons (28) are provided in an angularly spaced array about the longitudinal axis defined by handle assembly (20). The configuration and arrangement of buttons (28) in the present example enables an operator to easily access and actuate at least one button (28) regardless of the angular orientation of handle assembly (20) in the operator's hand. In other words, the operator will be able to easily actuate at least one button (28) with the thumb or index finger of the operator's hand that is grasping handle assembly (20) using a pencil grip. By way of example only, buttons (28) may be configured and operable in accordance with at least some of the teachings of U.S. Pat. app. Ser. No. 14/515,129, entitled "Activation Features for Ultrasonic Surgical Instrument," filed Oct. 15, 2014, issued as U.S Pat. No. 9,907,565 on Mar. 6, 2018, the disclosure of which is incorporated by reference herein. Alternatively, handle assembly (20) may have any other suitable user input features that are operable to selectively activate transducer assembly (30). As yet another merely illustrative alternative, transducer assembly (30) may be selectively activated using some other kind of user input (e.g., footswitch, etc.).

Figure 2:
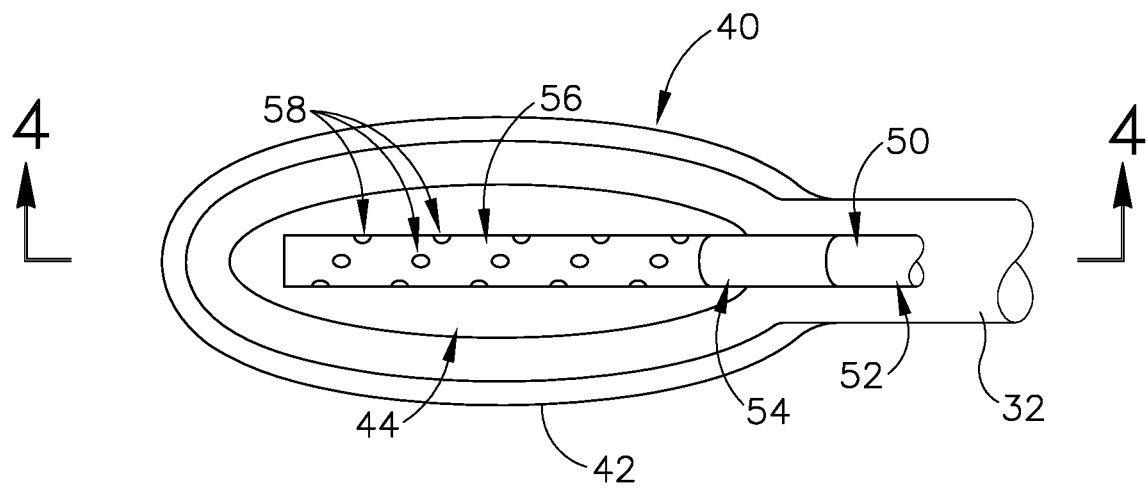
FIG. 2 depicts a top plan view of a working end of the instrument of FIG. 1.
Figure 3:
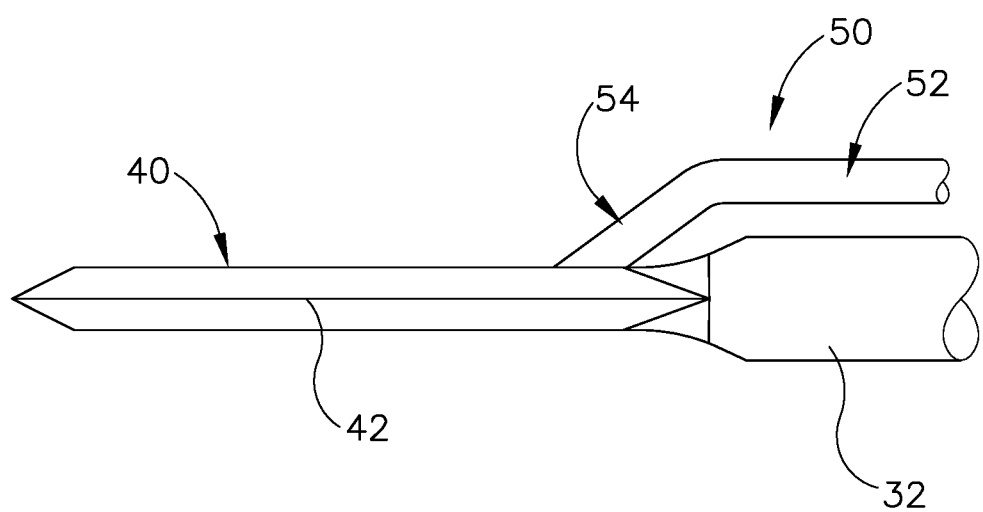
FIG. 3 depicts a side elevational view of the working end of FIG. 2.
Figure 4:
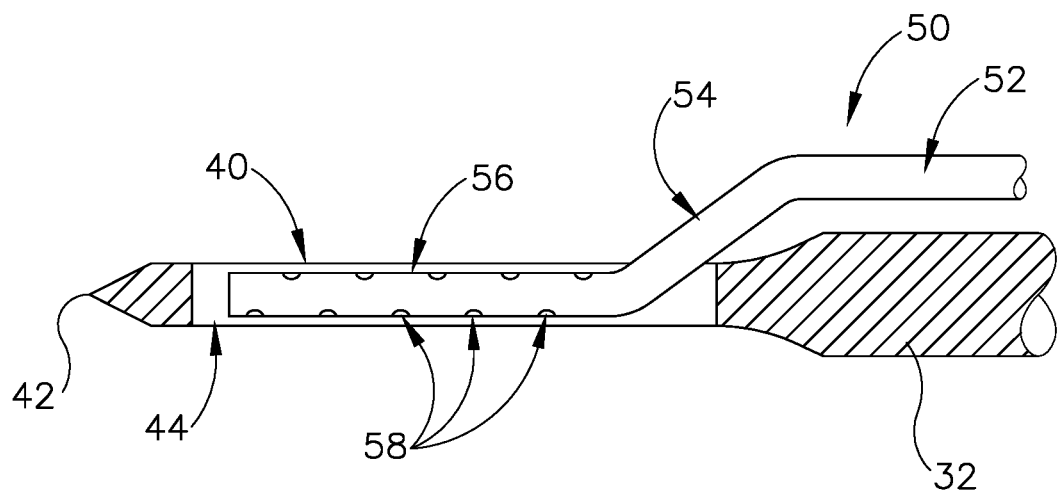
FIG. 4 depicts a cross-sectional side view of the working end of FIG. 2, taken along line 4-4 of FIG. 2.

As best seen in FIGS. 2-4, ultrasonic blade (40) of the present example includes a sharp edge (42) extending around the outer perimeter of blade (40). Ultrasonic blade (40) also defines an oblong transverse opening (44). Ultrasonic blade (40) thus has an elongate "O" shape or hollow elliptical shape in this example, similar to the head of a sewing needle (with opening (44) being similar to the eye of a sewing needle). Ultrasonic blade (40) is acoustically coupled with ultrasonic transducer assembly (30) via a waveguide (32), which extends through handle assembly (20) to join transducer assembly (30) with blade (40). Thus, ultrasonic vibrations that are generated by transducer assembly (30) are communicated along waveguide (32) to blade (40), such that blade (40) will vibrate ultrasonically when transducer assembly (30) is activated. Those of ordinary skill in the art will understand that, as a matter of physics, the distal end of blade (40) is located at a position corresponding to an anti-node associated with resonant ultrasonic vibrations communicated through waveguide (32) (i.e., at an acoustic anti-node).

When transducer assembly (30) is energized, the distal end of blade (40) is configured to move longitudinally in the range of, for example, approximately 10 to 500 microns peak-to-peak, and in some instances in the range of about 20 to about 200 microns at a predetermined vibratory frequency $f_o$ of, for example, approximately 21 kHz to approximately 31 kHz. In some other versions, the vibratory frequency is up to approximately 50 kHz or even up to approximately 55 kHz. At any such frequencies, when blade (40) is pressed against bone as described in greater detail below, the ultrasonic oscillation of blade (40) will work in concert with sharp edge (42) to break up the bone to promote cutting of the bone by blade (40).

Liquid dispensing feature (50) of the present example comprises a first longitudinally extending portion (52), an obliquely extending portion (54), and a second longitudinally extending portion (56). Portions (52, 54, 56) together defined a dogleg configuration. First longitudinally extending portion (52) is in fluid communication with fluid port (22), as selectively restricted by fluid switch (26). First longitudinally extending portion (52) is parallel to and offset from waveguide (32).

As best seen in FIG. 4, obliquely extending portion (54) is sized and configured to provide a transition whereby second longitudinally extending portion (56) is located within opening (44) defined by blade (40). Second longitudinally extending portion (56) extends along the same longitudinal axis as waveguide (32) in this example, though other configurations may be used if desired. Second longitudinally extending portion (56) defines a plurality of openings (58) that are in fluid communication with the interior of liquid dispensing feature (50). Openings (58) are discretely positioned in an array that extends along the length of second longitudinally extending portion (56) and about the longitudinal axis of second longitudinally extending portion (56). In the present example, openings (58) are formed as circular holes; though in other versions openings (58) may be in the form of elongate slots and/or have any other suitable configuration.

By way of example only, liquid dispensing feature (50) may be formed by a conventional hypotube that is bent to provide the dogleg configuration defined by portions (52, 54, 56). In some such versions, second longitudinally extending portion (56) is at least partially flattened along the same plane along which blade (40) extends. Other suitable ways in which liquid dispensing feature (50) may be formed will be apparent to those of ordinary skill in the art in view of the teachings herein. It should also be understood that no portions of liquid dispensing feature (50) contact blade (40) in this example. Moreover, liquid dispensing feature (50) has sufficient rigidity in this example such that liquid dispensing feature (50) will not contact blade (40) even if liquid dispensing feature (50) is pressed against bone or other structures during normal operation of instrument (10).

Figure 5:
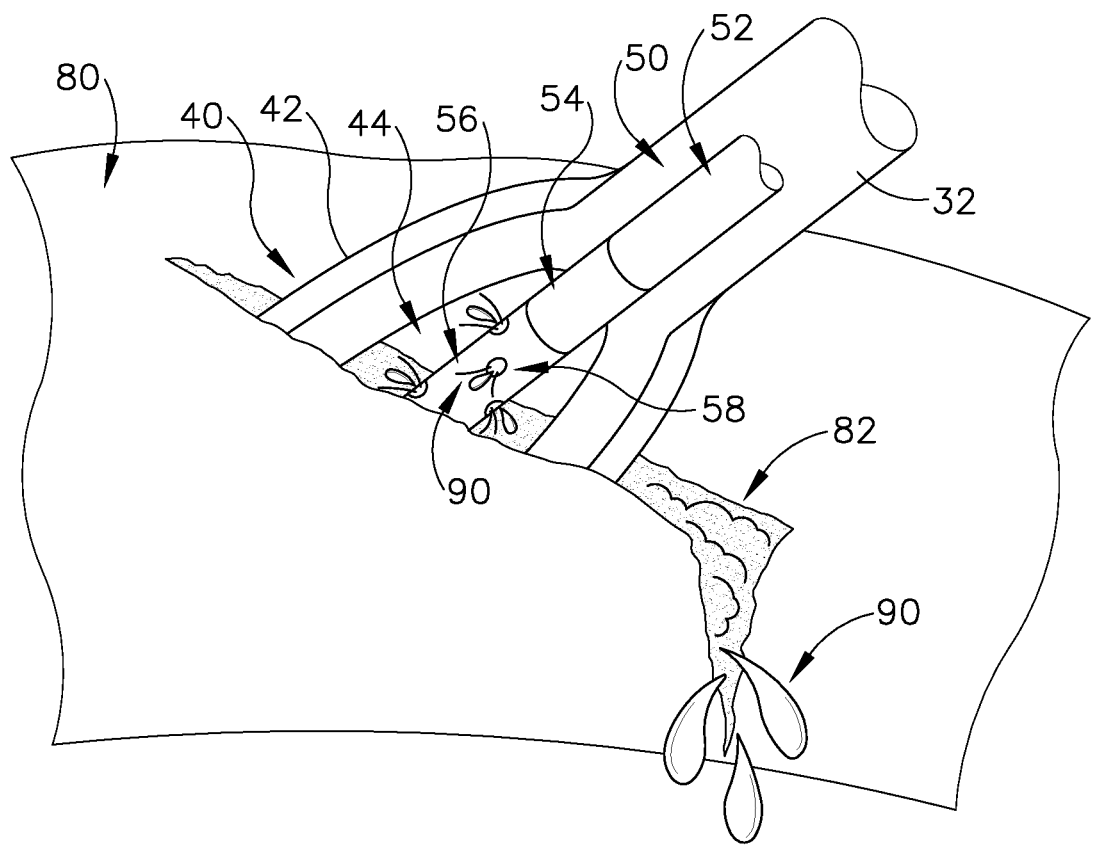
FIG. 5 depicts a perspective view of the working end of FIG. 2 cutting into bone and dispensing a cooling liquid to the cut site.
Figure 6:
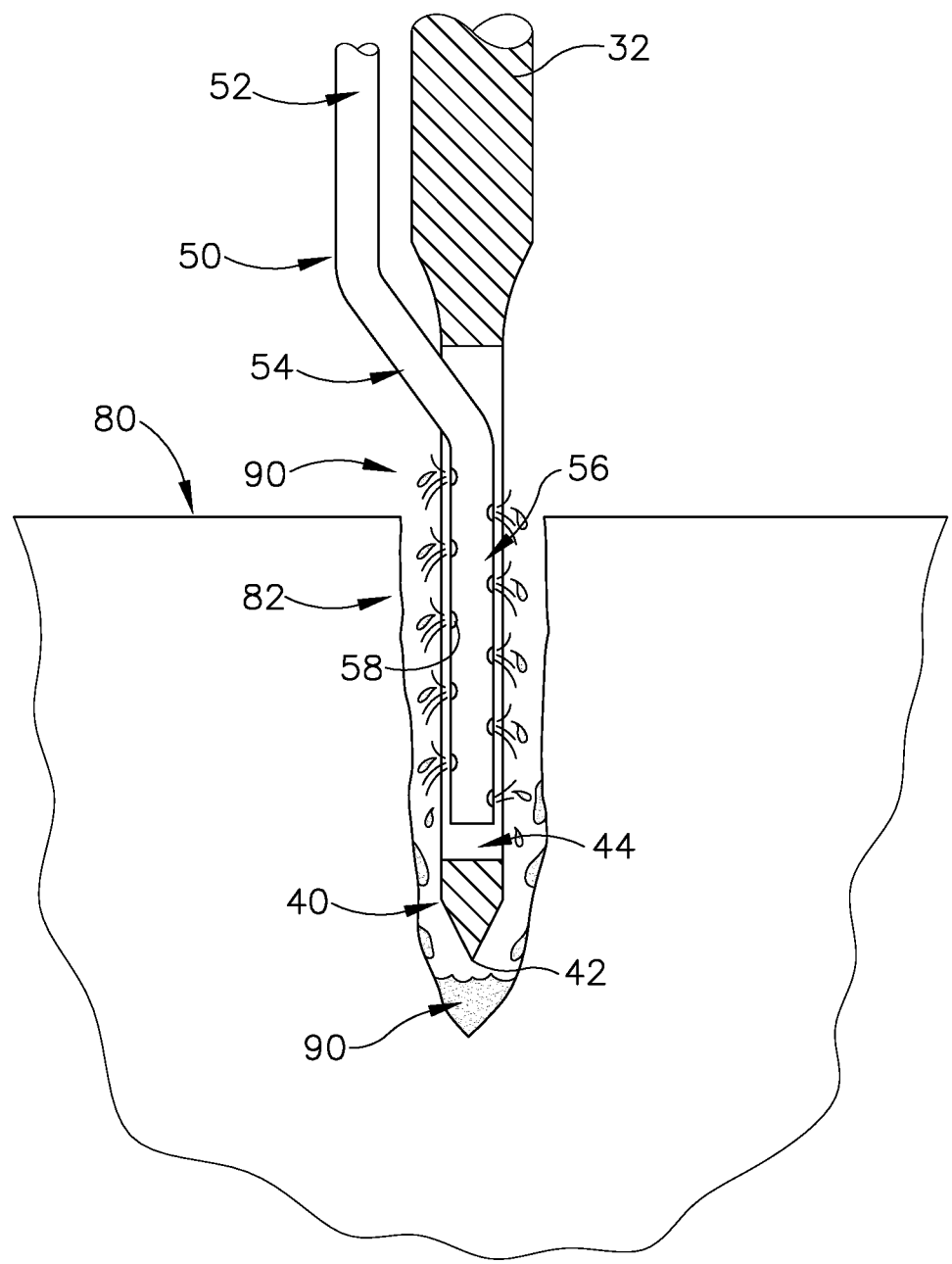
FIG. 6 depicts a cross-sectional side view of the working end of FIG. 2 disposed in bone and dispensing a cooling liquid to the cut site.

As noted above, when an ultrasonic blade is used to cut through bone, the friction caused by the blade vibrating against the bone may generate substantial heat, which may be undesirable. Thus, liquid dispensing feature (50) may be used to dispense fluid at a bone cut site in order to avoid having excess heat generated by blade (40). In particular, as shown in FIGS. 5-6, cooling liquid (90) may be dispensed via openings (58) in order to fill a cut site (82) with cooling liquid (90) as blade (40) cuts through bone (80). The dispensed cooling liquid (90) may directly contact blade (40) and the bone (80) at the cut site (82), thereby cooling blade (40) and the bone (80) at the cut site (82). It should be understood that the configuration of liquid dispensing feature (50) will dispense cooling liquid (90) at the distal end of blade (40) rather than simply dispensing the fluid proximal to blade (40). This may advantageously provide cooling at the region of blade (40) where the temperature is the highest. In addition or in the alternative, the distal location at which liquid dispensing feature (50) dispenses cooling liquid (90) may minimize the reduction of visibility of the surgical site that might otherwise be caused by cooling liquid (90).

As can be seen in FIGS. 3-6, second longitudinally extending portion (56) has a maximum thickness that is less than or equal to the maximum thickness of blade (40). As seen in FIGS. 5-6, this enables second longitudinally extending portion (56) to enter the cut (82) with blade (40). In other words, second longitudinally extending portion (56) and blade (40) can enter bone (80) together, without second longitudinally extending portion (56) getting snagged on bone (80) or otherwise interfering with entry of blade (40) into bone (80).

II. Exemplary Ultrasonic Surgical Instrument with Translating Liquid Cooling Feature having Blade Cooling Chamber When a cooling liquid (90) is delivered to a site where an ultrasonic blade (40) is vibrating, the vibrations of blade (40) may cause splashing of the cooling liquid (90). This may result in undesirable dispersal of the cooling liquid (90), which may adversely affect the cooling efficiency of the cooling liquid (90). It may therefore be desirable to provide a feature that minimizes splashing and keeps the cooling liquid (90) as close to blade (40) as possible. Moreover, it may be desirable to provide this same effect regardless of the degree to which blade (40) is disposed in bone (80).

Figure 7:
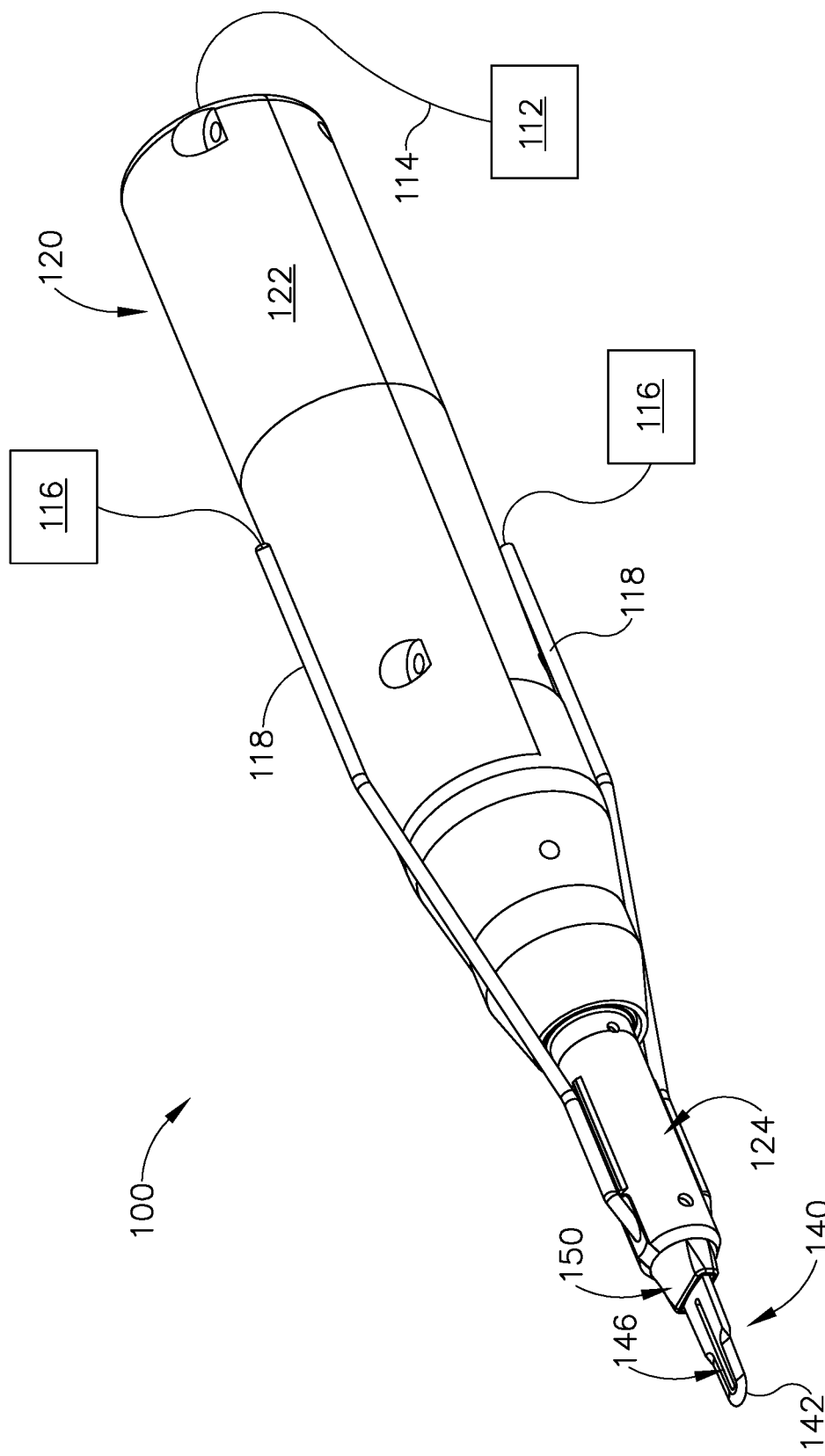
FIG. 7 depicts a perspective view of another exemplary ultrasonic surgical instrument.
Figure 8:
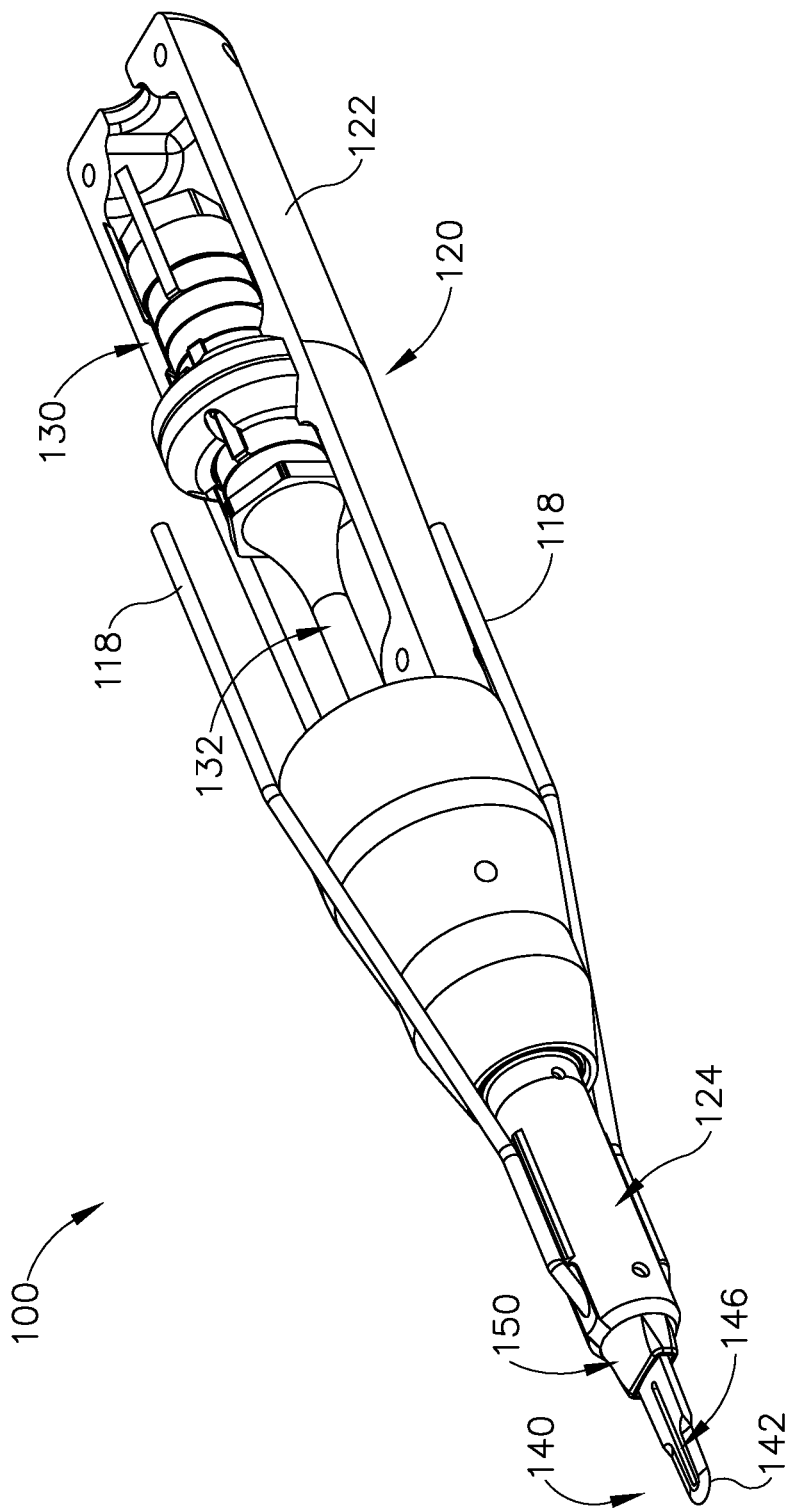
FIG. 8 depicts a perspective view of the instrument of FIG. 7, with a housing portion omitted to reveal internal components.

FIGS. 7 shows an exemplary alternative ultrasonic surgical instrument (100) that is configured to minimize splashing of cleaning fluid (90). Instrument (100) of this example comprises a handle assembly (120), an ultrasonic blade (140), and a liquid dispensing feature (150). Handle assembly (120) of this example includes housings (122) and a distal nose portion (124). As shown in FIG. 8, housings (122) contain a transducer assembly (130) and an acoustic waveguide (132), which is in acoustic communication with transducer assembly (130). Referring back to FIG. 7, transducer assembly (130) may be coupled with a generator (112) via a cable (114). It should be understood that generator (112), transducer assembly (130), and waveguide (132) may be configured and operable substantially similarly to generator (12), transducer assembly (30), and waveguide (32) described above. Thus, further details of these components will not be repeated here. While not shown in FIGS. 7-8, it should be understood that handle assembly (120) may also include activation buttons similar to buttons (28) described above. Alternatively, instrument (100) may rely on any other kind of user input feature(s) to selectively activate transducer assembly (130).

Figure 9A:
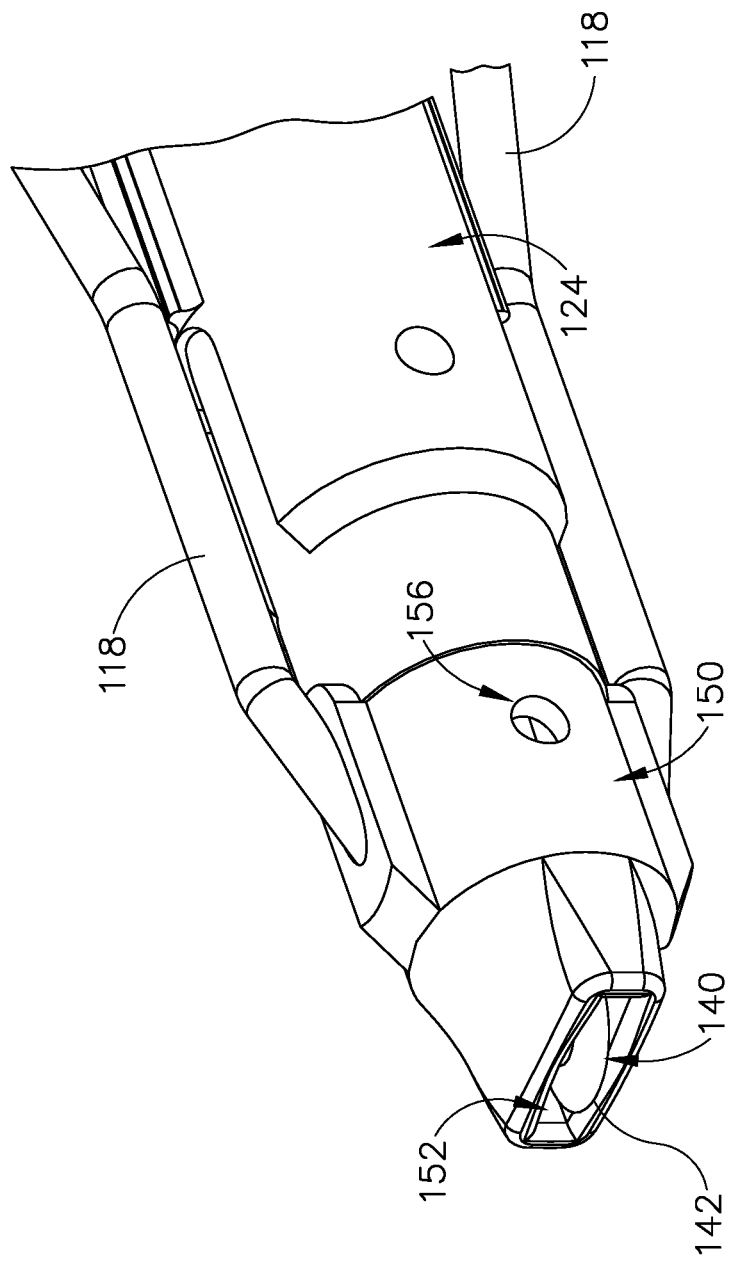
FIG. 9A depicts a perspective view of a working end of the instrument of FIG. 7, with a cooling sheath in a distal position.
Figure 9B:
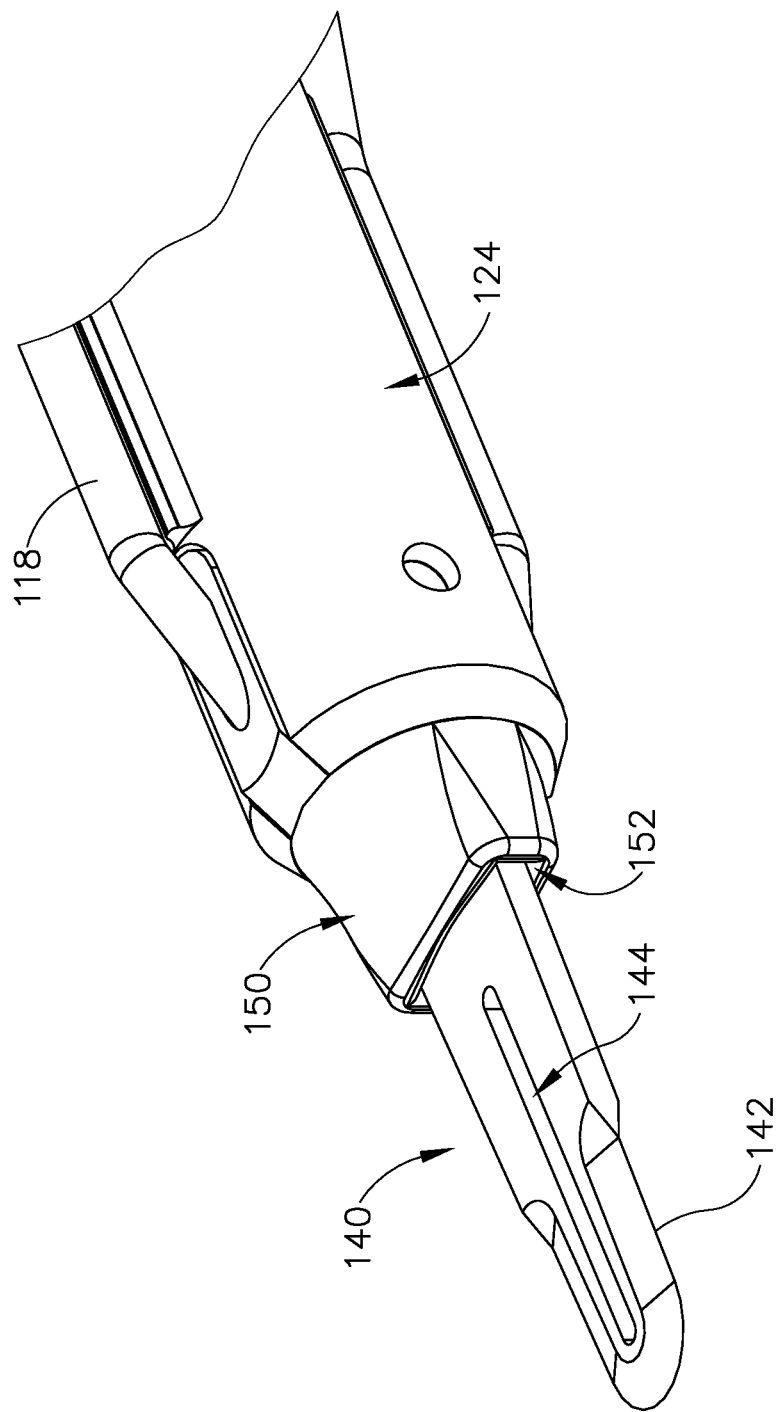
FIG. 9B depicts a perspective view of the working end of FIG. 9A, with the cooling sheath in a proximal position.

As best seen in FIG. 9B, ultrasonic blade (140) of the present example comprises a sharp cutting edge (142) and an oblong transverse opening (144). In the present example, transverse opening (144) passes completely through ultrasonic blade (140), from one transverse surface to an opposite transverse surface. Transverse opening (144) is configured to promote the communication of cooling liquid (90) through blade (140). In some other versions, transverse opening (144) is replaced with a recess or gutter. In such versions, recesses or gutters may be formed on both sides of ultrasonic blade (140). Such recesses or gutters may be configured to promote the communication of cooling liquid (90) along blade (140). Still other variations of blade (140) may include a combination of a transverse opening (144) and recesses or gutters, etc. Other suitable features and configurations that may be used to promote the communication of cooling liquid (90) through and/or along blade (140) will be apparent to those of ordinary skill in the art in view of the teachings herein.

Figure 10:
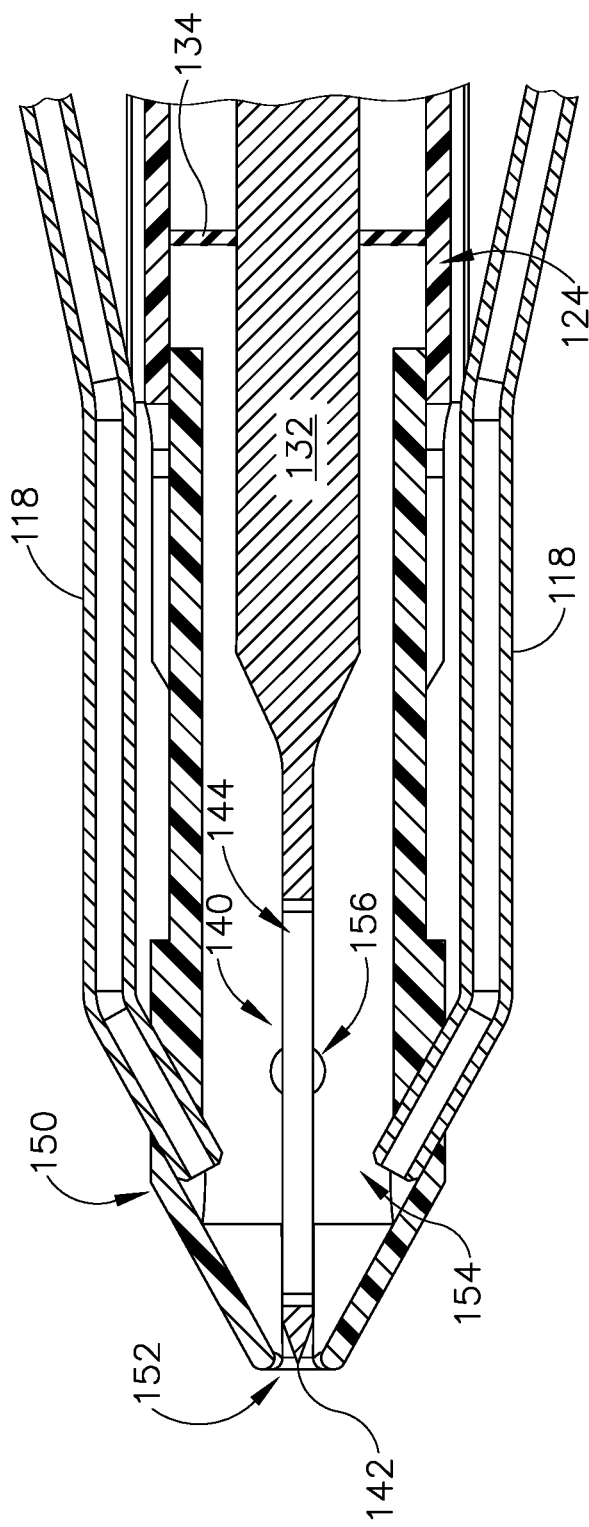
FIG. 10 depicts a cross-sectional side view of the working end of FIG. 9A, with the cooling sheath in the distal position.

Liquid dispensing feature (150) of the present example is configured to transition between a distal position (as shown in FIGS. 9A, 10, and 11A) and a proximal position (as shown in FIGS. 7-8, 9B, and 11B). When liquid dispensing feature (150) is in the distal position, liquid dispensing feature (150) fully encompasses (or at least substantially encompasses) blade (140). When liquid dispensing feature (150) is in the proximal position, blade (140) is fully exposed (or at least substantially exposed) relative to liquid dispensing feature (150). In the present example, liquid dispensing feature (150) is resiliently biased toward the distal position (e.g., by a coil spring, by a leaf spring, or by some other resilient feature). Liquid dispensing feature (150) will thus remain in the distal position unless and until the distal end of liquid dispensing feature (150) is acted upon by some other structure, such as a surface of bone (80) as described in greater detail below.

Liquid dispensing feature (150) is coupled with a pair of fluid conduits (118), which are further coupled with fluid sources (116). Fluid sources (116) and conduits (118) may be configured and operable just like fluid source (16) and conduit (18) described above. While two fluid sources (116) are shown in FIG. 7, it should be understood that both conduits (118) may instead be coupled with a single, shared fluid source (116). It should also be understood that conduits (118) are configured to translate with liquid dispensing feature (150) as liquid dispensing feature (150) translates between the distal and proximal positions. As best seen in FIG. 10, conduits (118) are in fluid communication with a hollow interior (154) defined by liquid dispensing feature (150). Thus, as fluid is communicated from fluid source (116) through conduits (118), this fluid will flood hollow interior (154). As also shown in FIG. 10, blade (140) is positioned in hollow interior (154) when liquid dispensing feature (150) is in the distal position. Blade (140) will thus be bathed in the cooling liquid within hollow interior (154) when liquid dispensing feature (150) is in the distal position as cooling liquid is communicated through conduits (118).

As shown in FIG. 9A, liquid dispensing feature (150) also includes a transverse opening (156) in this example. Transverse opening (156) is configured to allow some cooling liquid to escape from hollow interior (154). In some versions, more than one transverse opening (156) is included. In some other versions, transverse opening (156) is omitted.

In the present example, and as shown in FIG. 10, a seal (134) is positioned between waveguide (124) and distal nose portion (124). Seal (134) is configured to prevent the cooling liquid from traveling proximally along waveguide (132) into interior regions of handle assembly (120). Seal (134) may be positioned at a position corresponding to a node associated with ultrasonic vibrations communicated along waveguide (132). Various suitable ways in which seal (134) may be configured will be apparent to those of ordinary skill in the art in view of the teachings herein.

As best seen in FIGS. 9A-10, liquid dispensing feature (150) further includes a distal opening (152) that is sized to accommodate blade (140). In particular, distal opening (152) is large enough such that liquid dispensing feature (150) does not contact blade (140) throughout the longitudinal range of travel of liquid dispensing feature (150) relative to blade (140). Distal opening (152) is also large enough to allow cooling liquid to pass through distal opening (152) even while blade (140) is disposed in distal opening (152). Liquid dispensing feature (150) also has sufficient rigidity and support such that liquid dispensing feature (150) will not bend or otherwise deflect into contact with blade (140) even as transversely oriented forces impinge against liquid dispensing feature (150) (e.g., by liquid dispensing feature (150) being pressed against an anatomical structure) during normal operation of instrument (100).

FIGS. 11A-11B illustrate a sequence of an exemplary use of instrument (100). As shown in FIG. 11A, instrument (100) is initially positioned such that the distal end of liquid dispensing feature (150) is in contact with the outer surface of bone (80). At this stage, liquid dispensing feature (150) is in a distal position relative to blade (140). Blade (140) is thus fully recessed (or at least substantially recessed) relative to the distal end of liquid dispensing feature (150). The operator then activates blade (140) and begins communicating cooling liquid (90) to liquid dispensing feature (150), while simultaneously urging blade (140) distally into bone (80). As shown in FIG. 11B, sharp edge (142) of blade (140) and the ultrasonic vibration of blade (140) cooperate to form a cut (82) in bone (80). The distal end of liquid dispensing feature (150) remains in contact with the outer surface of bone (80), such that liquid dispensing feature (150) is now in a proximal position relative to blade (140). During the transition from the state shown in FIG. 11A to the state shown in FIG. 11B, cooling liquid (90) is communicated through liquid dispensing feature (150) in order to provide cooling to blade (140) and bone (80). As seen in FIG. 11B, cooling liquid (90) flows along blade (140) and along the cut (82) of the bone (80), reaching the distal end of blade (140). When the operator retracts instrument (100) proximally relative to bone (80) after forming cut (82), the bias of the resilient member (not shown) that acts against liquid dispensing feature (150) will return liquid dispensing feature (150) back to the distal position shown in FIG. 11A.

It should be understood from the foregoing that the translation of liquid dispensing feature (150) relative to blade (140) may assist in substantially containing cooling liquid (90) to thereby minimize splashing of cooling liquid, while still allowing blade (140) to enter bone (80). While liquid dispensing feature (150) translates relative to blade (140) in this example, some variations may provide a fixed version of liquid dispensing feature (150). For instance, in some alternative versions, liquid dispensing feature (150) may be fixedly secured to distal nose portion (124), such that liquid dispensing feature (150) does not translate relative to blade (140). In such alternative versions, liquid dispensing feature (150) may still dispense cooling liquid (90); and such cooling liquid (90) may still travel along blade (140) and into cut (82) to provide the cooling effects noted above. However, such versions may provide more splashing of cooling liquid (90) than the version described above with reference to FIGS. 7-11B.

Figure 12:
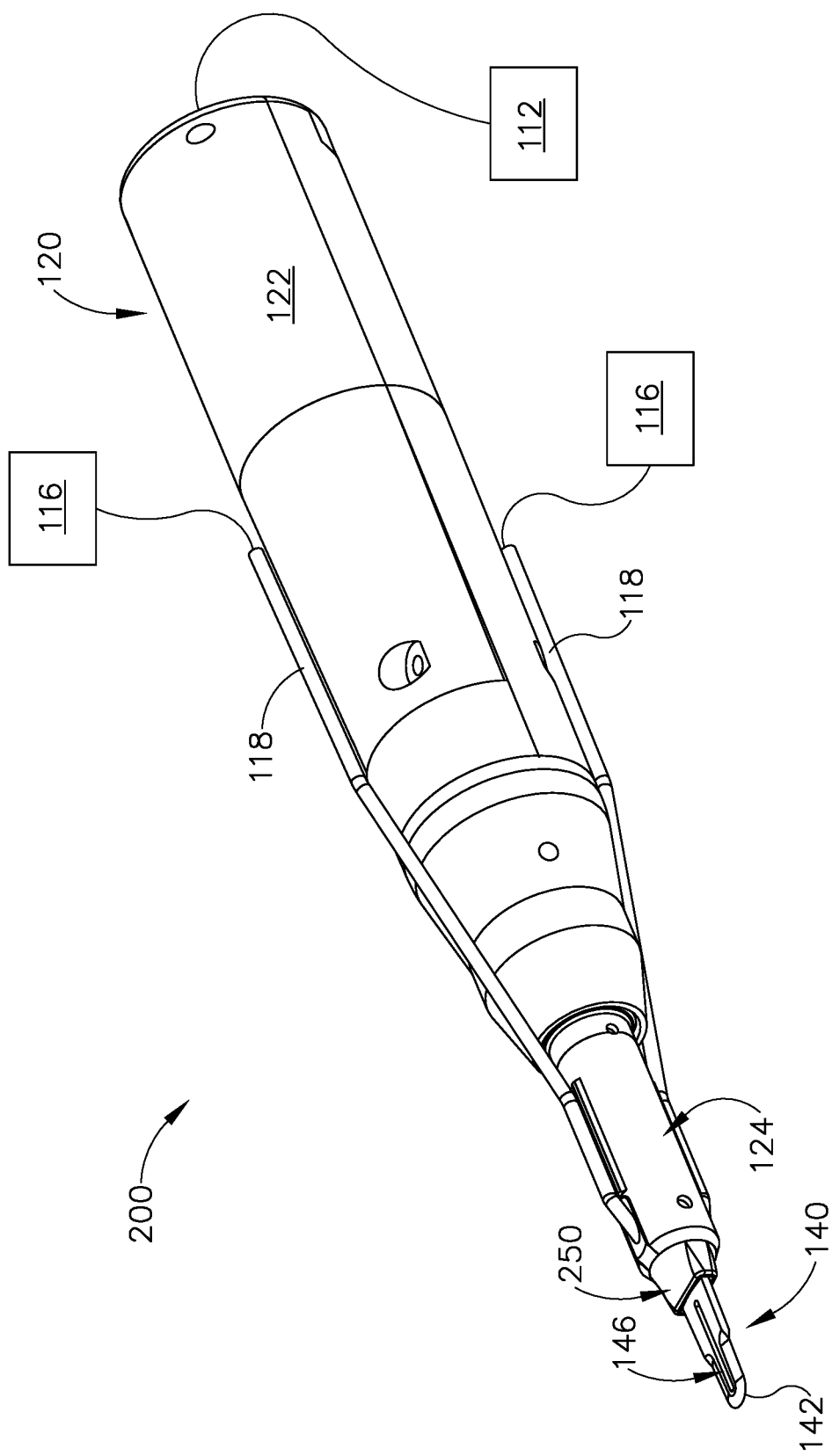
FIG. 12 depicts a perspective view of another exemplary ultrasonic surgical instrument.
Figure 13A:
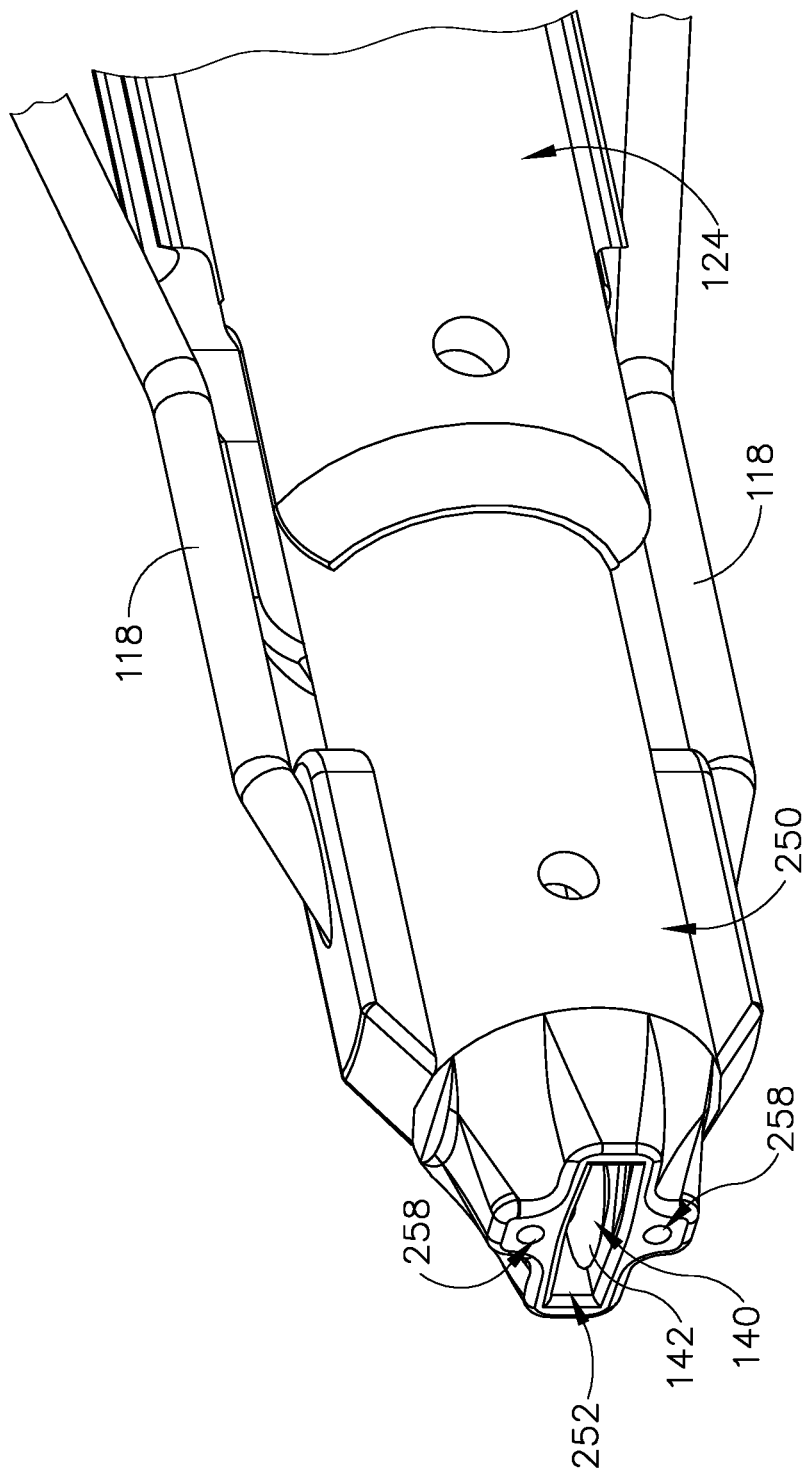
FIG. 13A depicts a perspective view of a working end of the instrument of FIG. 12, with a cooling sheath in a distal position.

III. Exemplary Ultrasonic Surgical Instrument with Translating Liquid Cooling Feature having Distal Cooling Jets FIGS. 12 shows another exemplary alternative ultrasonic surgical instrument (200) that is configured to provide liquid cooling. Instrument (200) of this example is substantially identical to instrument (100) described above, with the exception of the fact that instrument (200) has an alternative liquid dispensing feature (250) instead of having liquid dispensing feature (150). Otherwise, the same reference numbers are used in FIGS. 12-14 to indicate components that are identical to similarly numbered components from FIGS. 7-11B. The details of these identical components will therefore not be repeated here.

Figure 13B:
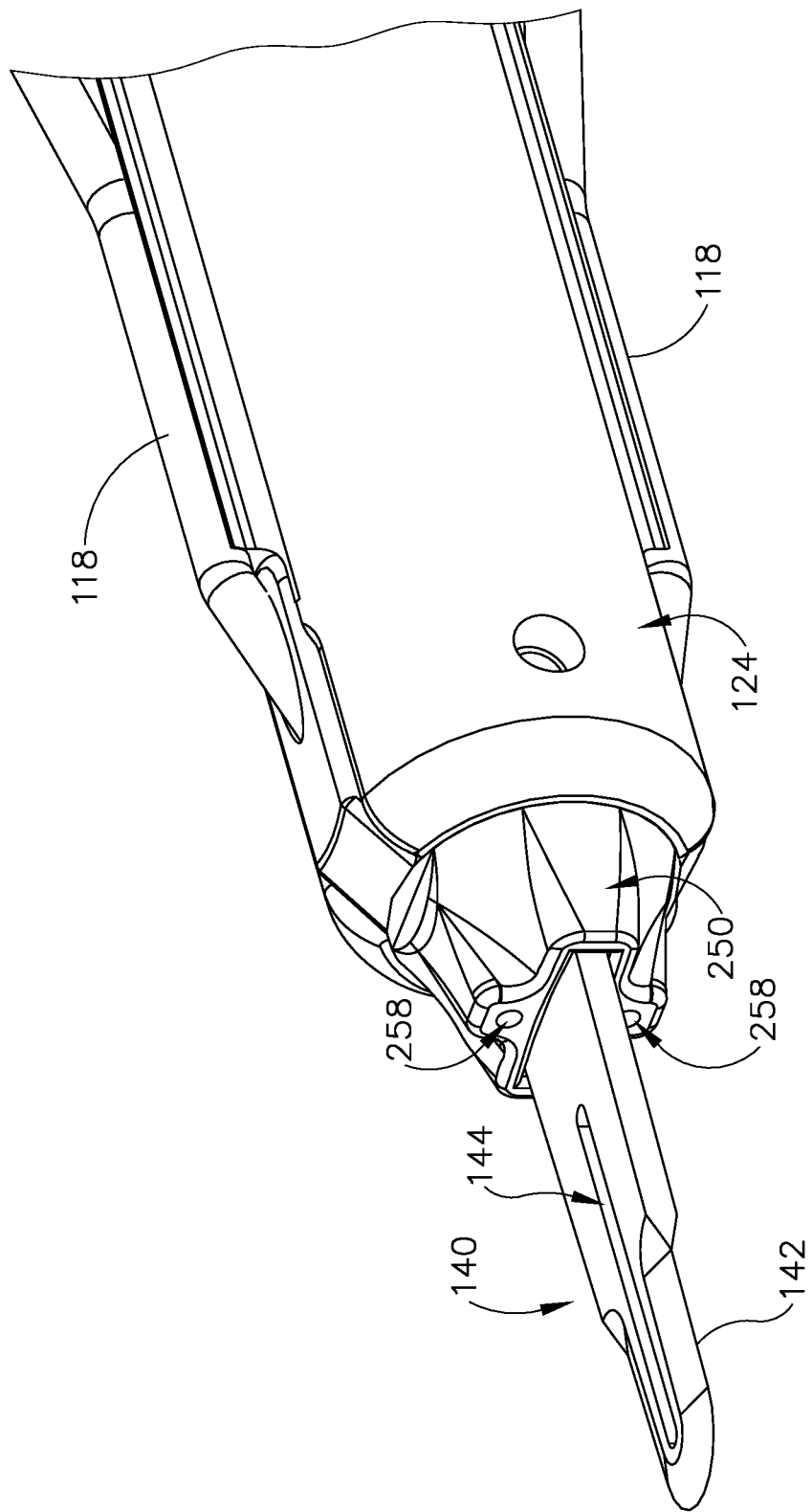
FIG. 13B depicts a perspective view of the working end of FIG. 13A, with the cooling sheath in a proximal position.
Figure 14:
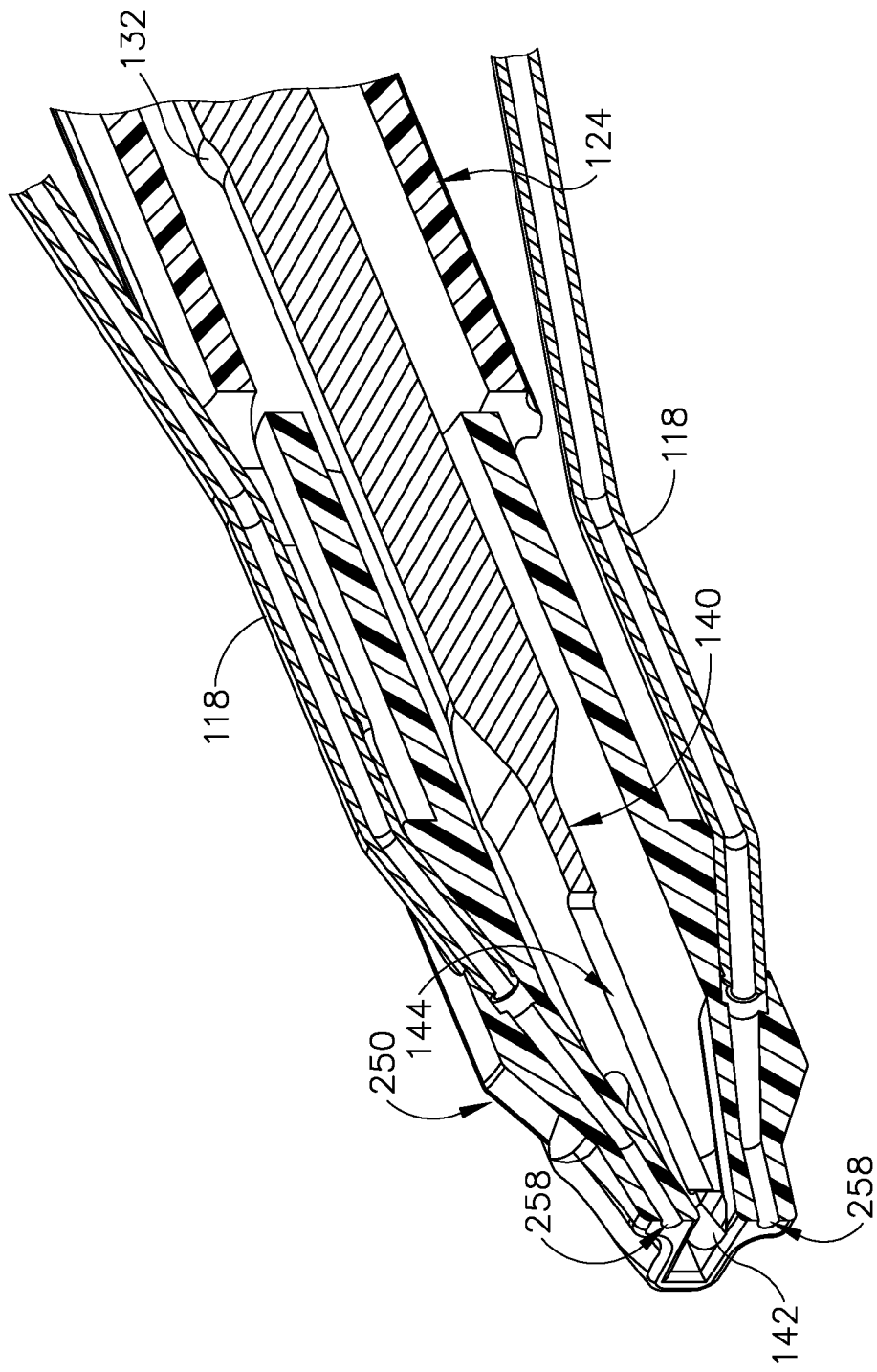
FIG. 14 depicts a cross-sectional perspective view of the working end of FIG. 13A, with the cooling sheath in the distal position.

Like liquid dispensing feature (150) described above, liquid dispensing feature (250) of the present example is configured to translate relative to blade (140) between a distal position (FIG. 13A) and a proximal position (FIG. 13B). Also as described above with respect to liquid dispensing feature (150), alternative versions of liquid dispensing feature (250) may be fixedly secured to distal nose portion (124), such that liquid dispensing feature (250) does not translate relative to blade (140). Unlike liquid dispensing feature (150) described above, liquid dispensing feature (250) of the present example includes a pair of cooling jet openings (258) located near distal opening (252). As best seen in FIG. 14, conduits (118) are in fluid communication with cooling jet openings (258). Thus, cooling liquid that is communicated from fluid sources (116) via conduits (118) will be further communicated through cooling jet openings (258). It should be understood that, cooling liquid (90) expelled through cooling jet openings (258) may provide a cooling effect to blade (140) and the bone (80) that is cut by blade (140), similar to the cooling effect described above. In some variations of liquid dispensing feature (250), liquid dispensing feature (250) is further configured to communicate cooling liquid to a hollow interior region of liquid dispensing feature (250), to thereby further cool a portion of blade (140) that is disposed in the hollow interior region. It should be understood that the cooling liquid may be communicated to this hollow interior region in addition to being communicated through cooling jet openings (258).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus comprising: (a) a body assembly; (b) an acoustic waveguide; (c) an ultrasonic blade positioned distally relative to the body assembly, wherein the ultrasonic blade is in acoustic communication with the acoustic waveguide; and (d) a liquid dispensing feature positioned distally relative to the body assembly, wherein the liquid dispensing feature is positioned adjacent to the ultrasonic blade, wherein the liquid dispensing feature is configured to deliver a flow of cooling liquid to the ultrasonic blade.

EXAMPLE 2

The apparatus of Example 1, wherein the ultrasonic blade defines a longitudinal axis, wherein at least a portion of the liquid dispensing feature extends along a path that is parallel to the longitudinal axis.

EXAMPLE 3

The apparatus of Example 2, wherein the liquid dispensing feature comprises: (i) a first portion extending parallel to the longitudinal axis of the ultrasonic blade, wherein the first portion is offset from the longitudinal axis of the ultrasonic blade, (ii) a second portion extending along the longitudinal axis of the ultrasonic blade, and (iii) a third portion joining the first portion with the second portion.

EXAMPLE 4

The apparatus of Example 3, wherein the third portion extends along a path that is obliquely oriented relative to the longitudinal axis of the ultrasonic blade.

EXAMPLE 5

The apparatus of any one or more of Examples 3 through 4, wherein the ultrasonic blade defines an opening, wherein the second portion is positioned in the opening.

EXAMPLE 6

The apparatus of any one or more of Examples 3 through 5, wherein the second portion defines a plurality of openings, wherein the openings are configured to expel the cooling liquid.

EXAMPLE 7

The apparatus of any one or more of Examples 3 through 6, wherein the ultrasonic blade has a maximum thickness, wherein the second portion has a maximum thickness, wherein the maximum thickness of the second portion is less than or equal to the maximum thickness of the ultrasonic blade.

EXAMPLE 8

The apparatus of any one or more of Examples 1 through 7, wherein the ultrasonic blade has a sharp edge extending from a proximal region to a distal region and back to the proximal region.

EXAMPLE 9

The apparatus of Example 8, wherein the liquid dispensing feature has a distal end, wherein the distal end is proximal to the distal region of the ultrasonic blade.

EXAMPLE 10

The apparatus of any one or more of Examples 1 through 9, wherein the liquid dispensing feature is configured to surround at least a portion of the ultrasonic blade.

EXAMPLE 11

The apparatus of Example 10, wherein the liquid dispensing feature is configured to translate relative to the body assembly between a distal position and a proximal position.

EXAMPLE 12

The apparatus of Example 11, wherein the ultrasonic blade is configured to be contained in a hollow interior defined by the liquid dispensing feature when the liquid dispensing feature is in the distal position, wherein the ultrasonic blade is configured to be exposed distally relative to the liquid dispensing feature when the liquid dispensing feature is in the proximal position.

EXAMPLE 13

The apparatus of any one or more of Examples 11 through 12, wherein the liquid dispensing feature is resiliently biased toward the distal position.

EXAMPLE 14

The apparatus of any one or more of Examples 10 through 13, wherein at least a portion of the ultrasonic blade is disposed in a hollow interior defined by the liquid dispensing feature.

EXAMPLE 15

The apparatus of Example 14, wherein the liquid dispensing feature is configured to deliver a flow of cooling liquid to the hollow interior.

EXAMPLE 16

The apparatus of Example 15, wherein the liquid dispensing feature further defines a distal opening in fluid communication with the hollow interior, wherein the liquid dispensing feature is further configured to expel cooling liquid through the distal opening.

EXAMPLE 17

The apparatus of Example 16, wherein the ultrasonic blade is configured to pass through the distal opening.

EXAMPLE 18

The apparatus of any one or more of Examples 1 through 17, wherein the liquid dispensing feature comprises at least two cooling jet openings configured to expel a flow of cooling liquid to the ultrasonic blade.

EXAMPLE 19

An apparatus comprising: (a) a body assembly; (b) an acoustic waveguide; (c) an ultrasonic blade positioned distally relative to the body assembly, wherein the ultrasonic blade is in acoustic communication with the acoustic waveguide; and (d) a liquid dispensing feature configured to translate relative to the ultrasonic blade, wherein the liquid dispensing feature is configured to deliver a flow of cooling liquid to the ultrasonic blade while translating relative to the blade.

EXAMPLE 20

A method of using an ultrasonic surgical instrument to cut bone, the method comprising: (a) urging a sharp edge of an ultrasonic blade of the ultrasonic surgical instrument against bone while the ultrasonic blade is vibrating ultrasonically, thereby forming a cut in the bone; and (b) communicating a cooling liquid via a liquid dispensing feature of the ultrasonic surgical instrument, wherein the act of communicating a cooling liquid comprises: (i) cooling a distal end of the ultrasonic blade, and (ii) cooling the cut bone.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
 (a) a body assembly;
 (b) an acoustic waveguide;
 (c) an ultrasonic blade positioned distally relative to the body assembly, wherein the ultrasonic blade is in acoustic communication with the acoustic waveguide; wherein the ultrasonic blade defines an opening proximal to a distal end of the ultrasonic blade; and
 (d) a liquid dispensing feature positioned distally relative to the body assembly, wherein the liquid dispensing feature is positioned adjacent to the ultrasonic blade, wherein at least a portion of the liquid dispensing feature is positioned within the opening of the ultrasonic blade, wherein the liquid dispensing feature is configured to deliver a flow of cooling liquid to the ultrasonic blade.

2. The apparatus of claim 1, wherein the ultrasonic blade defines a longitudinal axis, wherein at least a portion of the liquid dispensing feature extends along a path that is parallel to the longitudinal axis.

3. The apparatus of claim 2, wherein the liquid dispensing feature comprises:
 (i) a first portion extending parallel to the longitudinal axis of the ultrasonic blade, wherein the first portion is offset from the longitudinal axis of the ultrasonic blade, (ii) a second portion extending along the longitudinal axis of the ultrasonic blade, and (iii) a third portion joining the first portion with the second portion.

4. The apparatus of claim 3, wherein the third portion extends along a path that is obliquely oriented relative to the longitudinal axis of the ultrasonic blade.

5. The apparatus of claim 3, wherein the second portion defines a plurality of openings, wherein the openings are configured to expel the cooling liquid.

6. The apparatus of claim 3, wherein the ultrasonic blade has a maximum thickness, wherein the second portion has a maximum thickness, wherein the maximum thickness of the second portion is less than or equal to the maximum thickness of the ultrasonic blade.

7. The apparatus of claim 3, wherein the liquid dispensing feature comprises a hypotube bent to form the first portion, second portion, and third portion.

8. The apparatus of claim 3, wherein the second portion of the liquid dispensing feature is flattened along a plane defined by a flattened portion of the ultrasonic blade along the longitudinal axis.

9. The apparatus of claim 1, wherein the ultrasonic blade has a sharp edge extending from a proximal region to a distal region and back to the proximal region.

10. The apparatus of claim 9, wherein the liquid dispensing feature has a distal end, wherein the distal end is proximal to the distal region of the ultrasonic blade.

11. The apparatus of claim 1, wherein the liquid dispensing feature comprises at least two cooling jet openings configured to expel a flow of cooling liquid to the ultrasonic blade.

12. The apparatus of claim 1, wherein the liquid dispensing feature is configured to deliver a flow of cooling liquid to a region of highest temperature of the ultrasonic blade.

13. The apparatus of claim 1, wherein the liquid dispensing feature is configured to deliver a flow of cooling liquid to a cut site.

14. The apparatus of claim 1, wherein the body assembly comprises a handle assembly configured to be gripped by an operator.

15. The apparatus of claim 1, wherein the body assembly further comprises a fluid port configured to enable fluid flow from a fluid source to the liquid dispensing feature.

16. The apparatus of claim 15, wherein the body assembly further comprises a fluid switch operable to selectively control fluid flow to the liquid dispensing feature.

17. The apparatus of claim 1, wherein an ultrasonic transducer assembly extends proximally from the body assembly, wherein the ultrasonic transducer assembly is in acoustic communication with the acoustic waveguide.

18. The apparatus of claim 17, wherein the body assembly comprises one or more buttons, wherein the ultrasonic transducer assembly is configured to be activated in response to actuation of the one or more buttons.

19. An apparatus comprising:

(a) a body assembly;

(b) an acoustic waveguide;

(c) an ultrasonic blade positioned distally relative to the body assembly, wherein the ultrasonic blade is in acoustic communication with the acoustic waveguide, wherein the ultrasonic blade comprises a substantially flat surface along an edge of the ultrasonic blade, wherein the ultrasonic blade comprises an opening through the surface; and (d) a liquid dispensing feature positioned distally relative to the body assembly, wherein the liquid dispensing feature is positioned adjacent to the ultrasonic blade, wherein a distal end of the liquid dispensing feature is positioned within the opening, wherein the liquid dispensing feature is configured to deliver a flow of cooling liquid to the ultrasonic blade.

* * * * *